United States Patent [19]
Cavalleri et al.

[11] 3,954,789
[45] May 4, 1976

[54] 2-NITROIMIDAZOLE DERIVATIVES

[75] Inventors: Bruno Cavalleri, Milan; Giancarlo Lancini, Pavia, both of Italy

[73] Assignee: Gruppo Lepetit S.p.A., Milan, Italy

[22] Filed: July 26, 1972

[21] Appl. No.: 275,415

[30] Foreign Application Priority Data
July 30, 1971   Italy .................................. 42978/71

[52] U.S. Cl. ............................ 260/309; 260/240 A; 260/306.8 D; 260/309.2; 424/270; 424/273
[51] Int. Cl.² ....................................... C07D 233/91
[58] Field of Search ................................... 260/309

[56] References Cited
UNITED STATES PATENTS

| | | | |
|---|---|---|---|
| 3,583,985 | 6/1971 | Bambury et al. .................. | 260/309 |
| 3,711,495 | 1/1973 | Kulsa et al. ........................ | 260/309 |

OTHER PUBLICATIONS
Cosar et al., *Arzneimittel–Forschung*, 1966, Vol. 16, pp. 23–29.
*Chemical Abstracts Eighth Collective Index*, Vols. 66–75, 1967–1971, Subjects Glucope — Indena pp. 15577S, 15582S and 15590S, (1973).

*Primary Examiner*—Natalie Trousof
*Attorney, Agent, or Firm*—Theodore Post; C. Kenneth Bjork

[57] ABSTRACT

2-Nitroimidazole derivatives of the general formula

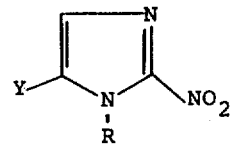

wherein R is a lower alkyl group and Y is a member of the group consisting of —CH₂OH, —CHO, CH₃CO—, vinyl, formylvinyl, styryl, substituted iminomethyl, 2-benzimidazolyl and 5-amino-1,3,4-thiadiazol-2-yl. The term "lower alkyl" designates aliphatic groups of from 1 to 4 carbon atoms; the term "substituted iminomethyl" designates nitrogen-containing functional derivatives of the aldehydic group. The compounds have antimicrobial activity.

4 Claims, No Drawings

2-NITROIMIDAZOLE DERIVATIVES

SUMMARY OF THE INVENTION

The present invention relates to 2-nitroimidazole derivatives and methods for their preparation. More particularly, the invention relates to 2-nitroimidazole derivatives of general formula

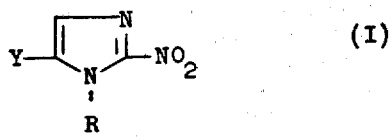

wherein R is a lower alkyl group and Y is a member of the group consisting of $-CH_2OH$, $-CHO$, $CH_3CO-$, vinyl, formylvinyl, styryl, substituted iminomethyl, 2-benzimidazolyl and 5-amino-1,3,4-thiadiazol-2-yl. The term lower alkyl designates aliphatic groups having from 1 to 4 carbon atoms, such as, for example, methyl, ethyl, propyl and butyl. The term substituted iminomethyl refers to imino functional derivatives of the aldehydic group such as, for example, the following derivatives of 1-lower alkyl-2-nitro-5-imidazolaldehyde: hydrazones, mono- and di-alkylhydrazones, aralkylhydrazones, cycloalkylhydrazones, mono- and di-arylhydrazones, hydroxyalkylhydrazones, acylhydrazones, semicarbazones, thiosemicarbazones, guanylhydrazones, oximes, substituted oximes, nitrones, aldazines, Schiff's bases, or substituted hydrazones in which the second nitrogen atom is a part of a 5 to 7 members heterocyclic ring, which may also contain other heteroatoms selected from N, O and S. The term "lower acyl" refers to acyl groups having from 2 to 4 carbon atoms. The present invention also relates to methods of preparation of the new 2-nitroimidazoles, as described below.

In general, the growth-inhibiting activity of the previously known nitroimidazoles was essentially limited to the protozoa, their activity against bacteria and fungi being quite poor. It has now been found surprisingly that the compounds of this invention possess a broad spectrum growth inhibiting activity toward gram-positive and gram-negative bacteria, fungi and protozoa. Particularly their inhibitory activity against *Clostridium perfringens*, *Salmonella typhi*, *Pseudomonas aeruginosa*, *Diplococcus pneumoniae*, *Streptococcus hemolyticus*, *E. coli* and *Mycobacterium tuberculosis* is noteworthy. In fact, it has been found that concentrations varying from about 0.5 to about 20 γ /ml. inhibit growth of these microorganisms in vitro. The compounds are active in the presence of bovine serum. In representative experiments, compounds of the general formula (I) such as, for instance, those described in Examples 1, 2, 3, 4, 6, 14 and 49 were found to be active also in the animals. Doses varying from about 50 to about 200 mg/kg p.o. are effective against experimental infection in mice from *Salmonella typhi*, *E. Coli* and *Diplococcus pneumoniae*. The compound of Example 60 was found to be active in mice infected with *Trichomonas vaginalis* at a dose of about 30 mg/kg p.o. The biological activity of the compounds is coupled with a low toxicity, since the $LD_{50}$ per os in mice is generally higher than 500 mg/kg.

DESCRIPTION OF THE PREFERRED EMBODIMENTS

The compounds of the invention are prepared by mixing a 1-lower alkyl-5-(2-chloroethyl)-2-nitroimidazole with a strong base such as, for example, an alkali metal hydroxide, a tertiary amine, an alkali metal lower alkoxide or an alkali metal amide in an inert organic solvent to obtain the corresponding 1-lower alkyl-5-vinyl-2-nitroimidazole. Other substituted 5-vinyl derivatives may be used as starting materials. Thus, for example, vinyl derivatives which are prepared by condensation of a 1-lower alkyl-5-methyl-2-nitroimidazole with an aliphatic, aromatic or heterocyclic aldehyde, in the presence of a strong base may be suitably utilized.

By oxidizing these vinyl compounds with potassium permanganate in a neutral solution or with osmium tetroxide, the corresponding 5-(1,2-dihydroxyethyl)-substituted compounds are obtained, which in turn may be converted into aldehydes by a subsequent oxidizing treatment. Suitable oxidizing agents for this latter step are sodium periodate and lead tetraacetate. The following typical scheme wherein X may be hydrogen, an alkyl, aryl or a heterocyclic moiety, illustrates such a process:

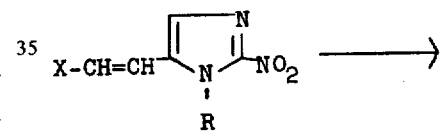

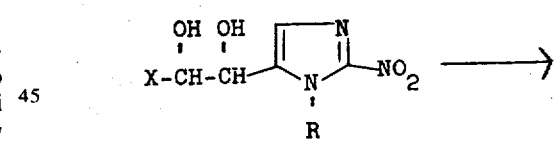

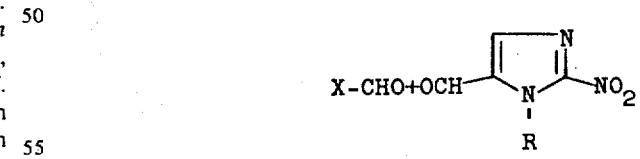

Alternatively, a 5-vinyl derivative of a 2-nitroimidazole may be directly oxidized to the corresponding aldehyde by treating it with sodium periodate in the presence of osmium tetroxide.

The derivatives wherein Y represents a $CH_2OH$ group may be obtained by reduction of the corresponding aldehyde with a metal hydride such as, for example, calcium borohydride or sodium borohydride.

Compounds in which Y is CH₃CO are obtained by treating the corresponding derivative in which Y is a CHO group with diazomethane in ethyl ether solution.

Another method for preparing a 2-nitroimidazolaldehyde of the present invention consists in the reduction with a mixed metal hydride of the carbalkoxy group of a 1-lower alkyl-5-carbalkoxy-2-nitroimidazole to give the corresponding alcohol. The alcoholic function is then oxidized to a 1-lower alkyl-2-nitro-5-imidazolaldehyde by oxidation with an agent selected from the group consisting of chromic acid, chromic anhydride and pyridine, manganese dioxide, lead tetraacetate or ceric salts.

The starting 1-lower alkyl-5-carbalkoxy-2-nitroimidazoles are obtained according to known procedures, using as the starting compounds cyanamide and an α-alkylaminoacetals containing a carbalkoxy group in a suitable position. Thus, for example, using α-methylamino-α-carbethoxyacetaldehyde diethylacetal and cyanamide, 2-amino-5-carbethoxy-1-methylimidazole is obtained, which is further transformed into the corresponding 2-nitro derivative by treatment with NaNO₂ according to the method of U.S. Pat. No. 3,420,842.

The compound of formula (I) wherein Y is a formylvinyl group is prepared from the nitroimidazole aldehydes by condensation with acetaldehyde in the presence of a basic catalyst such as an alkali hydroxide or an alkali metal alkoxide.

The method for preparing compounds wherein Y is a substituted iminomethyl group comprises treating a 1-lower alkyl-2-nitro-5-imidazolealdehyde with a suitable nitrogen-containing reactant of the carbonyl group such as amines, hydrazines and hydroxylamines or their acid salts in the presence of a solvent. The reaction is generally carried out at a temperature ranging between room temperature and the boiling point of the solvent. The solvent is advantageously selected from the lower alkanols, water and their mixtures. The proportions of the two reagents is not critical. Advantageously they are used in substantially equimolecular proportions of aldehyde and nitrogen compound, the proportions in which they react. If the nitrogen-containing reagent is employed in the form of a salt with an acid, the presence of at least one equimolecular amount of an acid acceptor is required.

The compounds wherein Y is a 2-benzimidazole radical are prepared by reaction of a selected nitroimidazolaldehyde with o-phenylenediamine, followed by a subsequent treatment with lead tetraacetate or other equivalent oxidizing agent such as, for example, atmospheric oxygen, mercuric oxide, manganese dioxide, potassium ferricyanide, a cupric salt and the like.

The compounds wherein Y is a 5-amino-1,3,4-thiadiazol-2-yl radical are prepared by oxidizing a thiosemicarbazone of a 1-lower alkyl-2-nitro-5-imidazolaldehyde with a ferric salt such as, for example, ferric chloride, calcium ferricyanide or ferric ammonium sulfate.

The following non-limitative examples illustrate the preparation of representative compounds falling within the scope of the present invention.

EXAMPLE 1:
α-(1-Methyl-2-nitroimidazole-5-yl)-N-methylnitrone

A mixture of 0.250 g. of 1-methyl-2-nitro-5-imidazolecarboxaldehyde, 0.150 g. of N-methylhydroxylamine hydrochloride and 0.150 g. of sodium bicarbonate is refluxed in 80 ml. of anhydrous ethanol for 2 hours and after filtration is concentrated to small volume. The title compound crystallizes on cooling. Yield: 0.24 g. m.p. 208°–209° C.

EXAMPLES 2–11:

Pursuant to the procedure of Example 1, an N-substituted hydroxylamine or its acid salt is reacted with a specified 1-lower alkyl-2-nitro-5-imidazolecarboxaldehyde to give the following nitrones. When an acid salt is employed, sodium bicarbonate, potassium acetate or triethylamine are added as acid acceptors. Melting points are in centigrade degrees.

2. α-(1-methyl-2-nitroimidazole-5-yl)-N-ethylnitrone, m.p. 138°–139°, by reacting 1-methyl-2-nitro-5-imidazolecarboxaldehyde with N-ethylhydroxylamine hydrochloride
3. α-(1-methyl-2-nitroimidazole-5-yl)-N-n-propylnitrone, m.p. 124°–126°, by reacting 1-methyl-2-nitro-5-imidazolecarboxaldehyde with N-(n-propyl)hydroxylamine hydrochloride
4. α-(1-methyl-2-nitroimidazole-5-yl)-N-isopropylnitrone, m.p. 125°–127°, by reacting 1-methyl-2-nitroimidazolecarboxaldehyde with N-isopropylhydroxylamine hydrochloride
5. α-(1-methyl-2-nitroimidazole-5-yl)-N-(2-hydroxyethyl)-nitrone, m.p. 210°–211°, by reacting 1-methyl-2-nitroimidazolecarboxaldehyde with N-(2-hydroxyethyl)-hydroxylamine hydrochloride
6. α-(1-methyl-2-nitroimidazole-5-yl)-N-(2-hydroxypropyl)-nitrone, m.p. 160°–161°, by reacting 1-methyl-2-nitro-5-imidazolecarboxaldehyde with N-(2-hydroxypropyl)-hydroxylamine hydrochloride
7. α-(1-methyl-2-nitroimidazole-5-yl)-N-phenylnitrone, m.p. 191°–192°, by reacting 1-methyl-2-nitro-5-imidazolecarboxaldehyde with N-phenylhydroxylamine hydrochloride.
8. α-(1-methyl-2-nitroimidazole-5-yl)-N-cyclohexyl-nitrone, m.p. 122°–123°, prepared by reacting 1-methyl-2-nitro-5-imidazolecarboxaldehyde with N-cyclohexylhydroxylamine hydrochloride
9. α-(1-methyl-2-nitroimidazole-5-yl)-N-(p-chlorophenyl)-nitrone, m.p. 195°–197°, prepared by reacting 1-methyl-2-nitro-5-imidazolecarboxaldehyde with N-(p-chlorophenyl)hydroxylamine hydrochloride
10. α-(1-ethyl-2-nitroimidazole-5-yl)-N-methylnitrone, m.p. 162°–163°, prepared by reacting 1-ethyl-2-nitro-5-imidazolecarboxaldehyde with N-methylhydroxylamine hydrochloride
11. α-(1-ethyl-2-nitroimidazole-5-yl)-N-(2-hydroxypropyl)-nitrone, m.p. 125°–128°, prepared by reacting 1-methyl-2-nitro-5-imidazolecarboxaldehyde with N-(2-hydroxypropyl)hydroxylamine hydrochloride

EXAMPLE 12:
1-Methyl-2-nitro-5-imidazolcarboxaldehyde oxime

To a solution of 0.400 g. of hydroxylamine hydrochloride in 15 ml. of methanol, 0.400 g. of 1-methyl-2-nitro-5-imidazolcarboxaldehyde in 20 ml. of ethanol and 0.810 ml. of triethylamine are added at room temperature. After standing overnight, the solution is concentrated to a small volume and the solid which precipitates is collected on the filter. After crystallization from water, 0.10 g. of the title compound is obtained which melts at 203°–205° C.

EXAMPLE 13:
1-Methyl-2-nitro-5-imidazolecarboxaldehyde O-decyloxime

To a solution of 0.3 g. of 1-methyl-2-nitro-5-imidazolecarboxaldehyde in 74 ml. of methanol, 0.335 g. of O-decylhydroxylamine is added. After standing overnight the title compound is recovered by filtration. Yield: 0.228 g., m.p. 70°C.

EXAMPLE 14:
1-Methyl-2-nitro-5-imidazolecarboxaldehyde thiosemicarbazone

A solution of 1.42 g. of thiosemicarbazide in water is added to a solution of 1.8 g. of 1-methyl-2-nitro-5-imidazolecarboxaldehyde in methanol. The solid which precipitates is recovered on the filter. Yield: 2.2 g., m.p. 282°–287°C.

EXAMPLE 15:
1-Ethyl-2-nitro-5-imidazolecarboxaldehyde thiosemicarbazone

The title compound is prepared by reacting 1-ethyl-2-nitro-5-imidazolealdehydecarboxaldehyde with thiosemicarbazide according to the procedure of the previous example. M.p. 220°–22°C.

EXAMPLE 16:
1-Methyl-5-[1-(2-hydroxyethyl)-5-ethyl-2-imidazolyl-]iminomethyl-2-nitroimidazole To a solution of 0.4 g. of 1-methyl-2-nitro-5-imidazolecarboxaldehyde dissolved in 25 ml. of ethanol, 0.494 g. of 1-(2-hydroxyethyl)-2-amino-5-ethylimidazole hydrochloride and 0.175 ml. of sodium ethoxide in 2.89 ml. of ethanol are added. After standing overnight, the solid which precipitates is collected on the filter and washed with water. Yield: 0.269 g., m.p. 185°–187°C.

EXAMPLE 17:
1-Methyl-2-nitro-5-imidazolecarboxaldehyde-2-hydroxyethylhydrazone A solution of 0.300 g. of 2-hydroxyethylhydrazine and 0.4 g. of 1-methyl-2-nitro-5-imidazolecarboxaldehyde in 20 ml. of methanol is allowed to stand for two days. The solid which precipitates is recovered on the filter and washed with water. Yield: 0.245 g., m.p. 138°–140°C.

EXAMPLES 18–48

By reacting a 1-lower alkyl-2-nitro-5-imidazole-carboxaldehyde with an amino compound having a free NH₂ group, as characterized below or its acid salt in the presence of an acid acceptor such as, for example, an alkali metal acetate, alkali metal bicarbonate, alkali metal carbonate, alkali metal hydroxide, alkali metal alkoxide, triethylamine, pyridine or the like, similarly to the procedure of Example 17, the following compounds are obtained. Their melting points are in centigrade degrees.

18. 1-methyl-2-nitro-5-imidazolecarboxaldehyde dimethylhydrazone, m.p. 133°–134°, by reacting 1-methyl-2-nitro-5-imidazolecarboxaldehyde with dimethyl hydrazine 19. 1-ethyl-2-nitro-5-imidazolecarboxaldehyde dimethylhydrazone, m.p. 80°–82°, by reacting 1-ethyl-2-nitro-5-imidazolecarboxyaldehyde with dimethyl hydrazine 20. 1-methyl-2-nitro-5-imidazolecarboxaldehyde phenylhydrazone, m.p. 220°–221°, by reacting 1-methyl-2-nitro-5-imidazolecarboxyaldehyde with phenyl hydrazine 21. 1-methyl-2-nitro-5-imidazolecarboxaldehyde 2,4-dinitrophenylhydrazone m.p. 276°–279°, by reacting 1-methyl-2-nitro-5-imidazolecarboxaldehyde with 2,4-dinitrophenyl hydrazine 22. 1-ethyl-2-nitro-5-imidazolecarboxaldehyde 2,4-dinitrophenylhydrazone, m.p. 215°–216°, by reacting 1-ethyl-2-nitro-5-imidazolecarboxaldehyde with 2,4-dinitrophenyl hydrazine 23. 1-methyl-2-nitro-5-imidazolecarboxaldehyde cyclopentylhydrazone, m.p. 135°–136°, by reacting 1-methyl-2-nitro-5-imidazolecarboxaldehyde with cyclopentylhydrazine 24. 1-ethyl-2-nitro-5-imidazolecarboxaldehyde 2-hydroxyethylhydrazone, m.p. 120°–121°, by reacting 1-methyl-2-nitro-5-imidazolecarboxaldehyde with 2-hydroxyethylhydrazine 25. 1-methyl-2-nitro-5-imidazolecarboxaldehyde acetylhydrazone, m.p. 224°–226°, by reacting 1-methyl-2-nitro-5-imidazolecarboxaldehyde with acetyl hydrazine 26. 1-methyl-2-nitro-5-imidazolecarboxaldehyde (cyanoacetyl)hydrazone, m.p. 232°–233°, by reacting 1-methyl-2-nitro-5imidazolecarboxaldehyde with (cyanoacetyl)hydrazine 27. 1-methyl-2-nitro-5-imidazolecarboxaldehyde ((trimethylammonio)acetyl)hydrazone chloride, m.p. 241°–242°, by reacting 1-methyl-2-nitro-5-imidazolecarboxaldehyde with ((trimethylammonio)acetyl)hydrazine chloride 28. 1-methyl-2-nitro-5-imidazolecarboxaldehyde (pyridinioacetyl)hydrazone chloride, m.p. 270°–271°, by reacting 1-methyl-2-nitro-5-imidazolecarboxaldehyde with (pyridinioacetyl)hydrazine chloride 29. 1-methyl-2-nitro-5-imidazolecarboxaldehyde 4-pyridylcarbonylhydrazone, m.p. 257°–258°, by reacting 1-methyl-2-nitro-5-imdazolecarboxaldehyde with 4-pyridylcarbonylhydrazine 30. 1-methyl-2-nitro-5-imidazolecarboxaldehyde hydrazone, m.p. 223°–224°, by reacting 1-methyl-2-nitro-5-imidazolecarboxaldehyde with hydrazine 31. 1-methyl-2-nitro-5-imidazolecarboxaldehyde 5-nitrofurfurylidenehydrazone, m.p. 247°–248°, by reacting 1-methyl-2-nitro-5-imidazolecarboxaldehyde with 5-nitrofurfurylidenehydrazine 32. 1-methyl-2-nitro-5-imidazolecarboxaldehyde hydrazone of 1-amino-4-methyl-piperazine m.p. 165°–167°, by reacting 1-methyl-2-nitro-5-imidazolecarboxaldehyde with 1-amino-4-methyl-piperazine 33. 1-methyl-2-nitro-5-imidazolecarboxaldehyde hydrazone of 1-amino-4-benzylpiperazine, m.p. 165°–168°, by reacting 1-methyl-2-nitro-5-imidazolecarboxaldehyde with 1-amino-4-benzyl-piperazine 34. 1-methyl-2-nitro-5-imidazolecarboxaldehyde hydrazone of 1-amino-3-hydroxypiperidine, m.p. 152°–153°, by reacting 1-methyl-2-nitro-5-imidazolecarboxaldehyde with 1-amino-3-hydroxypiperidine 35. 1-methyl-2-nitro-5-imidazolecarboxaldehyde hydrazone of 1-amino-tetrahydro-1,4-thiazine S-dioxide, m.p. 177°–179°, by reacting 1-methyl-2-nitro-5-imidazolecarboxaldehyde with 1-amino-tetrahydro-1,4-thiazine S-dioxide 36. 1-methyl-2-nitro-5-imidazolecarboxaldehyde carbamylhydrazone, m.p. 245°–246°, by reacting 1-methyl-2-nitro-5-imidazolecarboxaldehyde with carbamylhydrazine
37. 1-methyl-2-nitro-5-imidazolecarboxaldehyde 0-(2-hydroxyethyl)oxime, m.p. 95°–97°, by reacting 1-methyl-2-nitro-5-imidazolecarboxaldehyde with 0-(2-hydroxyethyl)hydroxylamine
38. 1-methyl-2-nitro-5-imidazolecarboxaldehyde hydrazone of 1-amino-hydantoin, m.p. 273°–274°, by reacting 1-methyl-2-nitro-5-imidazolecarboxaldehyde with 1-amino-hydantoin
39. 1-methyl-2-nitro-5-imidazolecarboxaldehyde hydrazone of 3-amino-5-(diethylaminomethyl)-2-oxazolidinone, m.p. 189°–190°, by reacting 1-methyl-2-nitro-5-imidazolecarboxaldehyde with 3-amino-5-(diethylaminomethyl)-2-oxazolidinone
40. 1-methyl-2-nitro-5-imidazolecarboxaldehyde p-hydroxyphenethylhydrazone, m.p. 221°–222°, by reacting 1-methyl-2-nitro-5-imidazolecarboxaldehyde with p-hydroxyphenethylhydrazine
41. 1-methyl-2-nitro-5-imidazolecarboxaldehyde 2,4,6-trichlorophenylhydrazone, m.p. 218°, by reacting 1-methyl-2-nitro-5-imidazolecarboxaldehyde with 2,4,6-trichlorophenylhydrazine
42. 1-methyl-2-nitro-5-imidazolecarboxaldehyde dodecylhydrazone, m.p. 122°–124°, by reacting 1-methyl-2-nitro-5-imidazolecarboxaldehyde with dodecylhydrazine
43. 1-methyl-2-nitro-5-imidazolecarboxaldehyde 4-allylthiosemicarbazone, m.p. 217°–218°, by reacting 1-methyl-2-nitro-5-imidazolecarboxaldehyde with 4allylthiosemicarbazide
44. 1-methyl-2-nitro-5-imidazolecarboxaldehyde p-(2-chloro-1,1,2-trifluoroethylsulfonyl)phenylhydrazone, m.p. 190°–193°, by reacting 1-methyl-2-nitro-5-imidazolecarboxaldehyde with p-(2-chloro-1,1,2-trifluoroethylsulfonyl)phenylhydrazine
45. 1-methyl-2-nitro-5-imidazolecarboxaldehyde p-fluorophenylhydrazone, m.p. 221°–222°, by reacting 1-methyl-2-nitro-5-imidazolecarboxaldehyde with p-fluorophenylhydrazine
46. 1-methyl-2-nitro-5-imidazolecarboxaldehyde 5-(2-chloroethyl)-1-n-propyl-2-imidazolylimine, m.p. 131°–132°, by reacting 1-methyl-2-nitro-5-imidazolecarboxaldehyde with 2-amino-5-(2-chloroethyl)-1-n-propyl-2-imidazolylimine
47. 1-methyl-2-nitro-5-imidazolecarboxaldehyde 1,5-dimethyl-2-imidazolylimine, m.p. 225°–227°, by reacting 1-methyl-2-nitro-5-imidazolecarboxaldehyde with 2-amino-1,5-dimethyl-2-imidazolylamine
48. 1-methyl-2-nitro-5-imidazolecarboxaldehyde 5-(3,4-dichlorophenyl)-2-imidazolylimine, m.p. 247° (dec.), by reacting 1-methyl-2-nitro-5-imidazolecarboxaldehyde with 2-amino-5-(3,4-dichlorophenyl)-2-imidazolylamine Pursuant to the procedures described in foregoing examples, many other compounds of formula (I) may be prepared, of which the following are representative.

a. 1-methyl-2-nitro-5-imidazolecarboxaldehyde 0-(2-phenoxyethyl)oxime
b. 1-methyl-2-nitro-5-imidazolecarboxaldehyde 0-(2-methoxyethyl)oxime
c. 1-methyl-2-nitro-5-imidazolecarboxaldehyde 0-(2-(2-ethoxyethoxy)ethyl)oxime
d. 1-methyl-2-nitro-5-imidazolecarboxaldehyde 0-(2-butoxyethyl)oxime
e. 1-ethyl-2-nitro-5-imidazolecarboxaldehyde 0-(7-phenoxyheptyl)oxime
f. 1-propyl-2-nitro-5-imidazolecarboxaldehyde thiosemicarbazone
g. 1-isopropyl-2-nitro-5-imidazolecarboxaldehyde methylnitrone
h. 1-methyl-2-nitro-5-imidazolecarboxaldehyde (2-ethoxyethyl)nitrone
i. 1-methyl-2-nitro-5-imidazolecarboxaldehyde 5-(p-chlorophenyl)-2-imidazolylimine
j. 1-methyl-2-nitro-5-imidazolecarboxaldehyde 5-(p-fluorophenyl)-2-imidazolylimine
k. 1-methyl-2-nitro-5-imidazolecarboxaldehyde 2-(carbethoxyethyl)nitrone
l. 1-methyl-2-nitro-5-imidazolecarboxaldehyde 2-acetoxyethyl)nitrone
m. 1-ethyl-2-nitro-5-imidazolecarboxaldehyde hydrazone of 1-amino-4-methylpiperazine
n. 1-methyl-2-nitro-5-imidazolecarboxaldehyde hydrazone of 1-aminopiperazine
o. 1-methyl-2-nitro-5-imidazolecarboxaldehyde 5-(4-biphenylyl)-2-imidazolylimine
p. 1-butyl-2-nitro-5-imidazolecarboxaldehyde ethylnitrone
q. 1-methyl-2-nitro-5-imidazolecarboxaldehyde allylnitrone
r. 1-methyl-2-nitro-5-imidazolecarboxaldehyde O-cyclopentyloxime
s. 1-methyl-2-nitro-5-imidazolecarboxaldehyde (p-methyoxyphenyl)nitrone
t. 1-methyl-2-nitro-5-imidazolecarboxaldehyde (3,4-dichlorophenyl)nitrone
u. 1-methyl-2-nitro-5-imidazolecarboxaldehyde (2-methoxyethyl)nitrone
v. 1-methyl-2-nitro-5-imidazolecarboxaldehyde 5-(2-naphthyl)-2-imidazolylimine

EXAMPLE 49:

2-Amino-5-(1-methyl-2-nitro-5-imidazolyl)-1,3,4-thiadiazole

2 Grams of 1-methyl-2-nitro-5-imidazolecarboxaldehyde thiosemicarbazone are added to a solution of 17.1 g. of $FeNH_4(SO_4)_2 \cdot 12H_2O$ in 35 ml. of water. The mixture is stirred at 80°–90°C. for 2 hours, and, after cooling, the solid product is collected on the filter and washed with water. The crude compound is crystallized from a mixture of methanol and dimethylformamide. Yield 0.95 g. (48%), m.p. 263°–265°C.

EXAMPLE 50:

5-(2-Benzylidimidazolyl)-1-methyl-2-nitroimidazole

A solution of 0.5 g. of 1-methyl-2-nitro-5-imidazolecarboxaldehyde and 0.348 g. of o-phenylenediamine in 10 ml. of ethanol is refluxed for two hours. The solid which precipitates is collected on the filter, washed with ethanol and dissolved in 10 ml. of acetic acid with the addition of 0.750 g. of $Pb(CH_3COO)_4$. The mixture is heated for 20 minutes at about 50°C., then cooled and diluted with 50 ml. of water. The resulting precipitate is collected on the filter and recrystallized from acetone, giving 0.15 g. of the title compound, m.p. 268°–270°C.

EXAMPLE 51: 1-Methyl-2-nitro-5-vinylimidazole

To a solution of 18.9 g. of 5-(2-chloroethyl)-1-methyl-2-nitroimidazole (prepared according to the procedure of British Pat. No. 1,222,486) in 2.8 liters of anhydrous benzene cooled to 5°–10°C., 16.8 g. of potassium tert-butoxide is added. Stirring is continued for 2 hours at 5°–10°C. After filtration and concentration to dryness under vacuum at a temperature lower than 50°C., the resulting yellow oily residue is washed three times with 50 ml. of ethyl ether (or light petroleum). The title product is obtained, which is dried under vacuum at 40°C.; yield 12 g. (77.7%). A sample crystallized from ethyl ether melts at 106°–108° C.

EXAMPLE 52:
1-Methyl-2-nitro-5-(1,2-dihydroxyethyl)-imidazole

To a solution of 6.2 g. of 1-methyl-2-nitro-5-vinylimidazole in 570 ml. of ethanol cooled to about −10°C., a solution of 5.46 g. of $KMnO_4$ and 8.85 g. of $MgSO_4.7H_2O$ in 750 ml. of $H_2O$ is added with stirring. The reaction mixture is filtered through Celite and washed with ethanol. The filtrate is concentrated to dryness under vacuum at 50° C., and the residue is taken up with acetone. The resulting solution is filtered and concentrated to dryness under vacuum. The resulting solid is crystallized from methyl ethyl ketone. Yield 3.15 g. (41.6%), m.p. 119°–121° C.

EXAMPLE 53:
1-Methyl-2-nitro-5-imidazolecarboxaldehyde

To a solution of 3.15 g. of 1-methyl-2-nitro-5-(1,2-dihydroxyethyl)imidazole in 200 ml. of methanol, a solution of 3.6 g. of $NaIO_4$ in 85 ml. of water is added with stirring. The precipitate which forms is filtered off and washed with methanol which is then added to the filtrate. By evaporation to dryness under vacuum a residue is obtained which is extracted several times with ethyl acetate. After concentration of the collected extracts, a crystalline product is obtained, which after recrystallization from ethyl acetate melts at 114°–115° C. Yield 2.5 g. (96%).

EXAMPLE 54: 1-Methyl-2-nitro-5-imidazolaldehyde

To a solution of 0.67 g. of 1-methyl-2-nitro-5-vinylimidazole in 20 ml. of 1,2-dimethoxyethane, a solution of 2 g. of $NaIO_4$ in 5 ml. of water, followed by 0.025 g. of $OsO_4$ is added with stirring at room temperature. After stirring for four hours, the mixture is allowed to stand overnight. The residue which is obtained by evaporation of the reaction medium to dryness under vacuum is extracted with ethyl acetate. The resulting solution after filtering is concentrated, yielding 0.43 3g. of a product which, after crystallization from ethyl acetate, melts at 114°–115°C. Yield 63%.

EXAMPLE 55: 1-Methyl-2-nitro-5-styrylimidazole

A mixture of 7.2 g. of 1,5-dimethyl-2-nitroimidazole, 41.2 ml. of benzaldehyde and 7.9 g. of potassium tert-butoxide in 300 ml. of ethanol is refluxed for 35 minutes under nitrogen. The residue, which is obtained by evaporation of the reaction mixture under vacuum, is extracted with ethyl ether and filtered. The ethyl ether solution after concentration yields an oily residue which is chromatographed through 300 g. of silica gel by eluting with chloroform. After evaporation of the solvent under vacuum at 40°C., an oily residue is obtained which crystallizes on standing. After washing with a small amount of methyl ethyl ketone, 1.9 g. (16%) of a product which melts at 170°–180°C. is obtained.

EXAMPLE 56: 1-Methyl-2-nitro-5-imidazolaldehyde

To a solution of 0.8 g. of 1-methyl-2-nitro-5-styrylimidazole in 300 ml. of methanol, a solution of 1.6 g. of $NaIO_4$ in 40 ml. of water, and 0.02 g. of $OsO_4$ are added. The mixture is stirred at room temperature for 10 hours, then an additional 0.01 g. of $OsO_4$ is added and stirring is carried on for 8 hours. The reaction mixture is filtered and evaporated to dryness under vacuum at room temperature. The residue is extracted with ethyl acetate. After concentration of the resulting solution, 0.325 g. of the product are obtained. Yield 60%.

EXAMPLE 57:
1-Methyl-2-nitro-5-hydroxymethylimidazole

To a solution of 1.55 g. of 1-methyl-2-nitro-5-imidazolecarboxaldehyde in 200 ml. of ethanol, a solution of 1.9 g. of $NaBH_4$ in 150 ml. of ethanol is added at about −4°C. After stirring for 15 minutes at 0°C., the excess of $NaBH_4$ is decomposed with 10% hydrochloric acid and the reaction mixture is filtered. the residue, which is obtained by evaporation of the filtrate, is crystallized from acetone and yield 1 g. of the title product which melts at 142°–144°C.

EXAMPLE 58:
2-Amino-5-carbethoxy-1-methylimidazole hydrochloride

Following the method described in U.S. Pat. No. 3,450,709 and starting from 10 g. of α-methylamino-α-carbethoxyacetaldehyde diethylacetal and 5.2 g. of cyanamide, 5.8 g. (62%) of 2-amino-5-carbethoxy-1-methylimidazole hydrochloride are obtained, which melts at 209°–211°C. after crystallization from isopropyl alcohol.

EXAMPLE 59:
5-Carbethoxy-1-methyl-2-nitroimidazole

Pursuant to the method described in U.S. Pat. No. 3,420,842 and starting from 6.8 g. of the product of the Example 58, 1.8 g. (27%) of 5-carbethoxy-1-methyl-2-nitroimidazole is obtained, which melts at 65°–66°C. after crystallization from hexane.

EXAMPLE 60:
1-Methyl-2-nitro-5-hydroxymethylimidazole

To 0.2 g. of 5-carbethoxy-1-methyl-2-nitroimidazole in 30 ml. of tetrahydrofuran, 0.044 g. of $LiBH_4$ is gradually added under stirring at room temperature. After stirring for 48 hours, the excess of $LiBH_4$ is decomposed with 10% hydrochloric acid, the reaction mixture is filtered and the filtrated is evaporated to dryness under vacuum. The residue is taken up with acetone. Inorganic salts are filtered off and the solution is evaporated. The oily residue is chromatographed through 7 g. of silica gel, by eluting with chloroform containing from 1% to 3% (v/v) of methanol. After concentration of the portions containing the product, 0.052 g. (33%) of 1-methyl-2-nitro-5-hydroxymethylimidazole is obtained.

EXAMPLE 61: 1-Methyl-2-nitro-5-imidazolaldehyde

To a solution of 0.15 g. of 1-methyl-2-nitro-5-hydroxymethylimidazole in 20 ml. of benzene, 0.33 g. of MnO₂ is added and the reaction mixture is heated on the steambath for 2 hours. After filtration and evaporation to dryness under vacuum, the crude product is crystallized from ethyl acetate and 0.060 g. (40.5%) of 1-methyl-2-nitro-5-imidazolaldehyde is obtained.

EXAMPLE 62: 5-Acetyl-1-methyl-2-nitroimidazole

To a solution of 0.70 g. of 1-methyl-2-nitro-5-imidazolecarboxaldehyde in 180 ml. of diethyl ether, a solution of 0.43 g. of diazomethane in 86 ml. of diethyl ether is added under cooling at about 0°C. After standing at room temperature for 7 days, the reaction mixture is filtered and then evaporated to dryness. The residue (0.60 g.), dissolved, in 6 ml. of chloroform, is chromatographed on 6 plates of silica gel, eluting with a 9:1 (v/v) chloroform:methanol mixture, and TLC spots are visualized under U.V. light. The silica gel, which corresponds to an Rf value from 0.64 up to 0.76 is collected and extracted with methanol. From this solution, after filtration and concentration, 0.065 g. of 5-acetyl-1-methyl-2-nitroimidazole is obtained, m.p. 81°–83°C.

EXAMPLE 63: 1-Ethyl-2-nitro-5-vinylimidazole

Pursuant to the same procedure described in Example 51, and using as starting material 2.2 g. of 5-(2-chloroethyl)-1-ethyl-2-nitroimidazole (prepared according to the method of British Pat. No. 1,222,486), 1.5 g. of the title compound is obtained, m.p. 45°–47°C.

EXAMPLE 64: 1-Ethyl-2-nitro-5-imidazolaldehyde

Following the same procedure described in Example 54 and using as a starting material 1.35 g. of 1-ethyl-2-nitro-5-imidazolaldehyde is obtained, m.p. 38°–40°C.

EXAMPLE 65: 1-Methyl-2-nitro-5-imidazoleacrolein

To a suspension of 1.5 g. of 1-methyl-2-nitro-5-imidazolecarboxaldehyde in 4.5 g. of acetaldehyde, 0.2 ml. of 25% KOH methanol solution is added at room temperature. Then 3 ml. of acetic anhydride is added and the mixture is refluxed for 20 minutes. After cooling, 9 ml. of water and 1.5 ml. of concentrated HCl acid are added to the mixture which is further refluxed for 30 minutes. Evaporation to dryness gives a residue which is taken up with hot ethyl acetate. The hot solution is filtered and the filtrate is concentrated in vacuo. The title compound crystallizes out on cooling. Yield 0.2 g., m.p. 165°–168°C.

EXAMPLE 66: 1-Ethyl-2-nitro-5-styrylimidazole

By reacting 0.33 g. of 1-ethyl-5-methyl-2-nitroimidazole with benzaldehyde according to the procedure of Example 55, 0.030 g. of 1-ethyl-2-nitro-5-styrylimidazole is obtained, m.p. 154°–156°C.

We claim:
1. A compound of the group consisting of 1-methyl-2-nitro-5-imidazolecarboxaldehyde, 1-ethyl-2-nitro-5-imidazolecarboxaldehyde and a-(1-methyl-2-nitro-5-imidazolyl)-N-methylnitrone.
2. A compound of claim 1 which is 1-methyl-2-nitro-5-imidazolecarboxaldehyde.
3. A compound of claim 1 which is 1-ethyl-2-nitro-5-imidazolecarboxaldehyde.
4. A compound of claim 1 which is α-(1-methyl-2-nitro-5-imidazolyl)-N-methylnitrone.

* * * * *